US010251925B2

(12) United States Patent
Tam et al.

(10) Patent No.: US 10,251,925 B2
(45) Date of Patent: Apr. 9, 2019

(54) PHARMACEUTICAL COMPOSITION FOR DISSOLVING AND ELIMINATING PATHOLOGICAL TISSUES AND PATHOGENS AND ITS USAGE

(76) Inventors: Kuok Leong Tam, Macao (CN); Io Cheng Tam, Macao (CN); Io Man Tam, Macao (CN)

( * ) Notice: Subject to any disclaimer, the term of this patent is extended or adjusted under 35 U.S.C. 154(b) by 93 days.

(21) Appl. No.: 13/392,267

(22) PCT Filed: Jun. 7, 2010

(86) PCT No.: PCT/CN2010/073628
§ 371 (c)(1),
(2), (4) Date: Apr. 9, 2012

(87) PCT Pub. No.: WO2011/023013
PCT Pub. Date: Mar. 3, 2011

(65) Prior Publication Data
US 2012/0189718 A1  Jul. 26, 2012

(30) Foreign Application Priority Data
Aug. 24, 2009  (CN) .......................... 2009 1 0042030

(51) Int. Cl.
| | | |
|---|---|---|
| *A61K 31/045* | (2006.01) | |
| *A61K 33/00* | (2006.01) | |
| *A61K 36/539* | (2006.01) | |
| *A61K 31/122* | (2006.01) | |
| *A61K 31/245* | (2006.01) | |
| *A61K 31/353* | (2006.01) | |
| *A61K 31/4375* | (2006.01) | |
| *A61K 36/484* | (2006.01) | |
| *A61K 36/534* | (2006.01) | |
| *A61K 36/708* | (2006.01) | |
| *A61K 36/756* | (2006.01) | |
| *A61K 35/65* | (2015.01) | |

(52) U.S. Cl.
CPC .......... *A61K 36/539* (2013.01); *A61K 31/045* (2013.01); *A61K 31/122* (2013.01); *A61K 31/245* (2013.01); *A61K 31/353* (2013.01); *A61K 31/4375* (2013.01); *A61K 33/00* (2013.01); *A61K 35/65* (2013.01); *A61K 36/484* (2013.01); *A61K 36/534* (2013.01); *A61K 36/708* (2013.01); *A61K 36/756* (2013.01)

(58) Field of Classification Search
CPC .................................................. A61K 36/539
USPC ........................................................ 424/401
See application file for complete search history.

(56) References Cited

U.S. PATENT DOCUMENTS

| | | | | |
|---|---|---|---|---|
| 4,055,660 A | * | 10/1977 | Meierhenry | 514/535 |
| 4,952,564 A | * | 8/1990 | Sato | A61K 31/12 514/533 |
| 5,433,950 A | * | 7/1995 | Popp | 424/400 |
| 7,572,469 B2 | * | 8/2009 | Santo | A61K 31/10 424/756 |
| 7,670,620 B2 | * | 3/2010 | Meisner | A61K 31/4745 424/475 |
| 7,994,141 B2 | * | 8/2011 | Park | A61K 8/0212 514/25 |
| 8,535,738 B2 | * | 9/2013 | Collins | A61K 8/347 424/735 |
| 2008/0031929 A1 | * | 2/2008 | Baggett | A61K 31/765 424/443 |
| 2008/0275077 A1 | * | 11/2008 | Skwierczynski et al. | 514/293 |

FOREIGN PATENT DOCUMENTS

| | | | |
|---|---|---|---|
| CN | 1269225 A | * 10/2000 | |
| CN | 101433617 | 5/2009 | |
| WO | WO 2009097512 A1 | * 8/2009 | A61K 36/236 |

OTHER PUBLICATIONS

Xiang, G., "Nevus eliminating ointment", CN 1269225 A, Oct. 2000, machine translation.*
Tan, G. et al., "A cream for dissolving warts, relieving neoplasm and detoxicating", May 20, 2009, CN101433617 A, English translation (PTO 14-3778).*
Yang, D. et al., "Study on the inhibitory activity, in vitro, of baicalein and baicalin against skin fungal and bacteria", Zhong Yao Cai, May 2000, 23(5): 272-4, abstract.*
Yamamoto, S. et al., "The potent anti-tumor-promoting agent isoliquiritigenin", Carcinogenesis, Feb. 1991; 12(2):31;7-23, abstract.*
International Search Report for international application No. PCT/CN2010/073628, dated Sep. 30, 2010 (5 pages).

* cited by examiner

*Primary Examiner* — Gina C Justice
(74) *Attorney, Agent, or Firm* — Hamre, Schumann, Mueller & Larson, P.C.

(57) ABSTRACT

A pharmaceutical composition for dissolving and eliminating wart and excrescence consisting of protein is disclosed in the present invention. The pharmaceutical composition comprises (in 100 weight parts) 1.0-60.0 parts of sodium hydroxide and/or potassium hydroxide. The pharmaceutical composition further comprises 0.25-1.0 parts of tetracaine, bufalin, venenum bufonis and/or menthol having local anesthetic effect. The pharmaceutical composition can dissolve and eliminate wart and excrescence consisting of protein immediately and has significant effect and low side effect.

6 Claims, No Drawings

PHARMACEUTICAL COMPOSITION FOR DISSOLVING AND ELIMINATING PATHOLOGICAL TISSUES AND PATHOGENS AND ITS USAGE

FIELD OF THE INVENTION

The present invention relates to a pharmaceutical composition for dissolving and eliminating pathological tissues and/or pathogens and its usage. More specifically the present invention relates to a pharmaceutical composition for external treating neoplasm, malignant hyperplasia, cellulitis sore, galls and warts, and irritating and itching scabies and dermatomycosis.

BACKGROUND OF THE INVENTION

According to description in Shennong's Herbal, which is the most existing earliest monograph of medicine in China, quicklime, or named as lime stone or calcium oxide, can be used to treat canker, scabies, malignant boil, mange, hemorrhoids, black mole and polyp. According to *Records of Famous Physicians* published near the end of Han Dynasty, quicklime can be used to treat necrosis. According to *Theory of Medicine Performance* written by Zhen Quan in Tang Dynasty, quicklime can be used to treat irritating scabies and malignant hyperplasia and used to stop incised wound from bleeding, which is not oral administrated and preferably mixed with egg white and caulis bambusae in taeniam. According to *Rihuazi Herbal* published in Song Dynasty, quicklime can used to promote healing and stop bleeding, especially to treat vitiligo, ulcer, scar, hemorrhoids, cellulitis sore, galls and warts. It can be seen that quicklime has been widely used in various dynasty in China to treat diseases associated with dampness, kill microbe, stop bleeding, relieve pain, and eliminate malignant hyperplasia, especially to treat scabies, wound bleeding, burned and scalded wound, hemorrhoids, archoptosis and excrescence.

SUMMARY OF THE INVENTION

The object of the present invention is to provide a pharmaceutical composition for rapidly dissolving and eliminating pathological tissues and pathogens as well as its usage based on folk nostrum and traditional Chinese medicine, especially based on the pharmacological effect of the alkaline property of quicklime and its clinical usage in folk nostrum and traditional Chinese medicine.

As one aspect of the present invention it provides a pharmaceutical composition for dissolving and eliminating pathological tissues and/or pathogens comprising 1.0-60.0 parts of sodium hydroxide and/or potassium hydroxide on the basis of 100.0 total weight parts with balance water.

Preferably, the pharmaceutical composition of the present invention can further comprises component(s) having local anesthetic effect, such as 0.25-1.0 parts of tetracaine, bufalin, venenum bufonis and/or menthol.

In one embodiment of the present invention, the pharmaceutical composition further comprises 0.01-0.5 parts of carbomer (941) as its excipient.

Preferably, the pharmaceutical composition of the present invention can be a complex preparation. For example, the pharmaceutical composition of the present invention can comprise 1.0-60.0 parts of sodium hydroxide and/or potassium hydroxide, 0-1.0 parts of menthol, 0-0.5 parts of isoliquiritigenin, 0-0.5 parts of baicalin, 0-0.5 parts of berberine, 0-0.5 parts of emodin and/or 0-0.5 parts of carbomer (941) as its excipient. More preferably, the pharmaceutical composition of the present invention can comprise 1.0-60.0 parts of sodium hydroxide and/or potassium hydroxide, 0.01-1.0 parts of menthol, 0.01-0.5 parts of isoliquiritigenin, 0.01-0.5 parts of baicalin, 0.01-0.5 parts of berberine, 0.01-0.5 parts of emodin and/or 0.01-0.5 parts of carbomer (941) as its excipient.

In the present invention the pharmaceutical composition can add hot water extracts of the following traditional Chinese medicine materials which are grinded into powder to form a complex preparation:

0-1.0 parts of mint, 0-3.0 parts of liquorice, 0-3.0 parts of baikal skullcap, 0-3.0 parts of Cortex Phellodendri and/or 0-3.0 parts of Radix ec Rhizoma Rhei; and more preferably, 0.01-1.0 parts of mint, 0.01-3.0 parts of liquorice, 0.01-3.0 parts of baikal skullcap, 0.01-3.0 parts of Cortex Phellodendri and/or 0.01-3.0 parts of Radix ec Rhizoma Rhei. Preferably the complex preparation comprises 0-0.5 parts of carbomer (941) as its excipient, and more preferably 0.01-0.5 arts of arbomer (941) as its excipient.

As another aspect of the present invention it also provides a usage of the above pharmaceutical composition to produce a medicine for rapidly dissolving and eliminating pathological tissues and pathogens.

Preferably, the present invention provides a usage of the above pharmaceutical composition to produce a medicine for rapidly dissolving and eliminating condyloma acuminatum (CA), molluscum contagiosum, skin cancer, polyps of various tissues and organs, precancerous lesion, prurigo nodularis, pigmentary naevus, corns, verruca vulgaris, or cutaneous tags.

In a further embodiment of the present invention, it provides a usage of the above pharmaceutical composition to produce a medicine for rapidly dissolving and eliminating sexually transmitted herpes, herpes zoster, rosacea, inflammatory acne, chronic cervicitis, hidradenitis suppurativa, abscess, furuncle and carbuncle, inflammatory granuloma, granuloma annulare, scabies, or sporotricosis.

In a further embodiment of the present invention, it provides a usage of the above pharmaceutical composition to produce a medicine for rapidly dissolving and eliminating verruca plana (flat warts), tuberculosis of skin, tuberculosis leprosy, seborrheic keratosis, or folliculitis.

In a further embodiment of the present invention, it provides a usage of the above pharmaceutical composition to produce a medicine for rapidly dissolving and eliminating tinea unguium, scleroderma, or dead skin.

In a further embodiment of the present invention, it provides a usage of the above pharmaceutical composition to produce a medicine for dissolving and eliminating neurodermatitis, pityriasis rosea, tinea corporis, or tinea pedis.

Based on folk nostrum and traditional Chinese medicines and combined with modern pharmacology, the present invention provides a pharmaceutical composition for rapidly dissolving and eliminating pathological tissues and pathogens with fast and significant curative efficacy, low side effect, and better promotion prospects.

The present invention will be further explained in details in connection with the following examples. But the present invention is not limited to the following examples. Any modification or equivalent based on the spirit of the present invention still belongs to the protection scope of the appended claims of the present invention.

PREFERRED EMBODIMENTS OF THE INVENTION

According to the present invention a pharmaceutical composition for dissolving and eliminating pathological tissues and pathogens comprises 1.0-60.0 parts of sodium hydroxide on the basis of 100.0 total weight parts with balance water.

Sodium hydroxide can be substituted by potassium hydroxide with same parts.

Sodium hydroxide can be also substituted by the mixture sodium hydroxide and potassium hydroxide with same parts.

Sodium hydroxide and potassium hydroxide can dissolve protein. With proper concentration they can rapidly dissolve and eliminate various pathological tissues and pathogens consisting of protein. And that is the basis of the present invention.

The pharmaceutical composition of the present invention can further comprise compounds having local anesthetic action to become a complex preparation. For example, the pharmaceutical composition can comprise 1.0 parts of tetracaine, 0.5 parts of bufalin, 0.75 parts of venenum bufonis or 1.0 parts of menthol. The patients treated by the pharmaceutical composition with be anesthetic compound(s) feel painless or less painful. The pharmaceutical composition of the present invention can further comprise 0-0.5 parts of carbomer (941) as its excipient.

The pharmaceutical composition of the present invention can further comprise Chinese medicine materials to become a complex preparation, e.g. 0-1.0 parts of menthol, 0-0.5 parts of isoliquiritigenin, 0-0.5 parts of baicalin, 0-0.5 parts of berberine, and/or 0-0.5 parts of emodin, as well as 0-0.5 parts of carbomer (941) as its excipient.

The pharmaceutical composition of the present invention can further comprise the powder of Chinese medicine materials or their hot water extracts to become a complex preparation, e.g. 0-1.0 parts of mint, 0-3.0 parts of liquorice, 0-3.0 parts of baikal skullcap, 0-3.0 parts of Cortex Phellodendri, and/or 0-3.0 parts of Radix ec Rhizoma Rhei, as well as 0-0.5 parts of carbomer (941) as its excipient.

In the above complex preparation liquorice (glycyrrhizic acid, isoliquiritigenin) has antibacterial, antiviral, antitumor, anti-inflammatory and immune-regulatory functions. Radix ec Rhizoma Rhei (emodin) has antibacterial, antiviral, anti-inflammatory, and antitumor functions. Baikal skullcap (baicalin) has antibacterial, antiviral, anti-allergic, and anti-cancer functions. Cortex Phellodendri (berberine) has antibacterial and anti-cancer functions. The above Chinese medicine materials or their active ingredients can be mixed together with sodium hydroxide or potassium hydroxide to form a complex preparation to enhance therapeutic efficacy.

Example 1

The medicine prepared in this example can be named Preparation I for dissolving and eliminating pathological tissues and pathogens, or ointment for dissolving and eliminating warts.

Based on weight parts, the pharmaceutical composition in this example comprises 20.0 parts of sodium hydroxide and 1.0 parts of tetracaine with addition of balance water to 100.0 parts.

The medicine prepared in this example has excellent performance for rapidly dissolving and eliminating pathological tissues and pathogens, particularly suitable for treating condyloma acuminatum (CA), molluscum contagiosum, skin cancer, polyps of various tissues and organs, precancerous lesion, prurigo nodularis, pigmentary naevus, corns, verruca vulgaris, or cutaneous tags.

In the art podophyllotoxin is the drug of first choice for treating condyloma acuminatum recommended by WHO and the Ministry of Public Health of the Peoples Republic of China. It is also the main component of the drug WARTREC YouDI produced by Stiefel of America and the drug YouDi produced by GuiZhou Hangfang of China. According to their specification these drugs will be topically applied to the afflicted area of a patient two times each in the morning and in the evening for consecutive three days until the wart becomes whitened. Then stop application and observe for 4 days, and each course of treatment will take 7 days. If the wart does not disappear in a first course of treatment then a second course of treatment starts, but total treating process should be no more than three courses of treatment (21 days).

Preparation I for dissolving and eliminating pathological tissues and pathogens of this example was applied to treat the wet condyloma acuminatum on inner prepatial lamina (including urethra), anus, and vulva (including cervix and vagina). Applied Preparation I with cotton swab. For condyloma acuminatum wart in size of peanut it was dissolved into a semi-transparent fluid in about ten minutes with a black kernel in one-third of its original size left. Such a black kernel was from capillary proliferation and hyperplasia in the dermis of condyloma acuminatum tissues which became black and atrophied affected by Preparation I. Wiped off the semi-transparent fluid and applied Preparation I several times. The black kernel was continuously dissolved, atrophied, or sloughed within 30 minutes. The injuries immediately became narrow and healed in several days. For condyloma acuminatum wart in small size it was better to apply Preparation I with bamboo toothpick and it was eliminated within several minutes.

Example 2

The medicine prepared in this example can be named Preparation II for dissolving and eliminating pathological tissues and pathogens, or ointment for immediately eliminating herpes.

Based on weight parts, the pharmaceutical composition in this example comprises 3.0 parts of liquorice, 3.0 parts of baikal skullcap, 3.0 parts of Cortex Phellodendri, 1.0 parts of Radix ec Rhizoma Rhei, 1.0 parts of mint, 2.5 parts of sodium hydroxide, 1.0 parts of venenum bufonis and 0.25 parts of carbomer (941) as its excipient with addition of balance water to 100.0 parts.

The components liquorice, baikal skullcap, Cortex Phellodendri, Radix ec Rhizoma Rhei, venenum bufonis, and mint are grinded into powder in size of 200 meshes.

Preparation II can also be applied to treat condyloma acuminatum. After applying Preparation I for dissolving and eliminating pathological tissues and pathogens to eliminate the large and small visible warts, then apply Preparation II for dissolving and eliminating pathological tissues and pathogens onto the affected areas and their surrounding areas for treating subclinical affected areas of CA in order to dissolve and eliminate all tiny affected areas and pathogens HPV virus and thus to reduce recurring. After 5 to 20 minutes wipe away the remaining drug with cotton ball absorbed with distilled water and stop treating.

Preparation I and Preparation II for dissolving and eliminating pathological tissues and pathogens can be used together to rapidly dissolve and eliminate condyloma acuminatum (including HPV virus within the warts), which is never been described in the art.

Take photos for each re-examination and input these photos into a computer for comparison and diagnostic. Observe these photos by enlarging them 10-50 times to determine whether a subclinical condition exists and to determine whether a further treatment is needed.

Preparation II for dissolving and eliminating pathological tissues and pathogens is suitable for treating sexually transmitted herpes, herpes zoster, rosacea, inflammatory acne, chronic cervicitis, hidradenitis suppurativa, abscess, furuncle and carbuncle, inflammatory granuloma, granuloma annulare, scabies, or sporotricosis. The advantage of this formulation is that it can be selectively to treat pathological tissues without injuring normal tissues if it is applied with proper times and duration.

For example, applied Preparation II to treat sexually transmitted herpes and/or herpes zoster on or around genitalia. Several minutes later the patient felt less painful and the fluid of the affected areas was absorbed out. In about ten minutes the patient did not feel painful anymore. The herpes disappeared within an average time of 18.77 minutes, from 5 minutes to 48 minutes. The average time of scabbing and healing was 26.11 hours, from 17 hours to 38 hours. Such an excellent effect is never recorded up to now in the art.

For example, applied Preparation II to treat rosacea and/or inflammatory acne. Several minutes later the pathological tissues started to dissolve, the sanies and fluid exuded, and the affected areas became narrow. Cleaned the exuded sanies and fluid, and repeated the above process 1-2 times. The affected areas rapidly disappeared and no exudation existed. Next day it scabbed and within 10-14 days it sloughed with growing new skin. For treating severe rosacea such as rhinophyma Preparation II could be applied with different areas and repeated several times. The neoplasm would be dissolved and eliminated from the outside to the inside. Such a treatment is not recorded in the literature, and the prior treatment can not reach such a rapid effect.

Example 3

The medicine prepared in this example can be named Preparation III for dissolving and eliminating pathological tissues and pathogens. Based on weight parts, the pharmaceutical composition in this example comprises 1.0 parts of glycyrrhizic acid, 1.0 parts of baicalin, 1.0 parts of berberine, 1.0 parts of emodin, 1.0 parts of menthol, 4.0 parts of sodium hydroxide (or potassium hydroxide), and 0.5 parts of venenum bufonis as well as 0.25 parts of carbomer (941) as its excipient with addition of balance water to 100.0 parts.

Preparation III is suitable for treating verruca plana (flat warts), tuberculosis of skin, tuberculosis leprosy, seborrheic keratosis, or folliculitis.

For example applied Preparation III to treat verruca plana (flat warts), molluscum contagiosum, seborrheic keratosis, and/or folliculitis with toothpick or cosmetic tips until the affected areas became black. Then wiped off the drug. When treating tuberculosis of skin and tuberculosis leprosy applied Preparation III onto the rash area. After several minutes the fluid exuded out and when wiped off the drug one could observe that the rash skin atrophied. Made the determination whether a further application of the drug was needed after a week. As a comparison it would become effective only after several months if these diseases were treated with antibiotics. Therefore Preparation III could substantially shorten the course of treatment. It could also be suitable to treat neurodermatitis, pityriasis rosea, tinea corporis, or tinea pedis.

Preparation III can be diluted with distilled water or mineral water to 1-10 times for externally treating small areas of burned or scalded injuries in degree I-II by washing or spreading the drug. It can rapidly relieve pain, kill virus and bacteria, de-blister and anti-infect.

Example 4

The medicine prepared in this example can be named Preparation IV for dissolving and eliminating pathological tissues and pathogens. Based on weight parts, the pharmaceutical composition in this example comprises 30.0 parts of sodium hydroxide (or potassium hydroxide) with addition of balance water to 100.0 parts.

Preparation IV can be externally applied to dissolve tinea unguium, scleroderma, or dead skin.

Preparation IV can also for be used to treat small or tiny affected areas which are less sensitive tissues for pain. When a patient has a general anesthesia or a local anesthesia for pathological tissues Preparation IV can also be locally applied to dissolve wider pathological tissues or more sensitive pathological tissues rapidly and thoroughly. Its usage and treating method can be referred to that of Preparation I for dissolving and eliminating pathological tissues and pathogens in Example 1.

The invention claimed is:

1. A method for dissolving and eliminating pathological tissues and/or pathogens, comprising:
    administering an effective amount of a pharmaceutical composition to a pathological tissue of a subject in need thereof,
    wherein on the basis of 100 weight parts of said pharmaceutical composition, the pharmaceutical composition consists of
    1.0-60.0 parts of at least one selected from the group consisting of sodium hydroxide and potassium hydroxide,
    at least one selected from the group consisting of 0.01-0.5 parts of isoliquiritigenin, 0.01-0.5 parts of baicalin, 0.01-0.5 parts of berberine, and 0.01-0.5 parts of emodin, and
    a balancing amount of an ingredient that is at least one selected from the group consisting of an excipient and a solvent.

2. The method according to claim 1, wherein the pathological tissues and/or pathogens include at least one selected from the group consisting of condyloma acuminatum (CA), molluscum contagiosum, skin cancer, polyps of various tissues and organs, precancerous lesion, prurigo nodularis, pigmentary naevus, corns, and cutaneous tags.

3. The method according to claim 1, wherein the pathological tissues and/or pathogens include at least one selected from the group consisting of tuberculosis of skin, tuberculosis leprosy, seborrheic keratosis and folliculitis.

4. The method according to claim 1, wherein the pathological tissues and/or pathogens include at least one selected from the group consisting of tinea unguium, scleroderma and dead skin.

5. The method of claim 1, wherein the pathological tissues and/or pathogens include condyloma acuminatum, sexually transmitted herpes, herpes zoster, rosacea, inflammatory acne, verruca plana, molluscum contagiosum, seborrheic keratosis, and/or folliculitis.

6. The method according to claim 1, wherein the ingredient is water.

* * * * *